United States Patent [19]

Winter, deceased et al.

[11] 4,364,400
[45] Dec. 21, 1982

[54] HETEROCYCLIC DERIVATIVES AS FLAVORING AGENTS

[75] Inventors: Max Winter, deceased, late of Vandoeuvres, Switzerland; by Pierre Mottu, executor, Geneva, Switzerland

[73] Assignee: Firmenich SA, Geneva, Switzerland

[21] Appl. No.: 173,290

[22] Filed: Jul. 29, 1980

Related U.S. Application Data

[60] Division of Ser. No. 907,828, May 19, 1978, Pat. No. 4,262,030, which is a division of Ser. No. 805,338, Jun. 10, 1977, Pat. No. 4,220,561, which is a continuation-in-part of Ser. No. 600,275, Jul. 31, 1975, abandoned.

[30] Foreign Application Priority Data

Aug. 2, 1974 [CH] Switzerland ............ 10619/74
Jan. 16, 1975 [CH] Switzerland ............ 520/75

[51] Int. Cl.$^3$ ............................................. A24B 15/40
[52] U.S. Cl. ............................................. 131/277
[58] Field of Search ............................ 131/274–279

*Primary Examiner*—V. Millin
*Attorney, Agent, or Firm*—Pennie & Edmonds

[57] ABSTRACT

1,3-Oxathiane and 1,3-oxathiolane derivatives, some which are new, are disclosed as being useful as perfuming and flavoring agents for the preparation of perfumes and perfumed articles and for the manufacture of artificial flavors, flavored foodstuffs, animal feeds, beverages, pharmaceutical preparations and tobacco products.

4 Claims, No Drawings

HETEROCYCLIC DERIVATIVES AS FLAVORING AGENTS

CROSS-REFERENCE TO RELATED APPLICATION

This is a division of application Ser. No. 907,828, filed May 19, 1978, now U.S. Pat. No. 4,262,030, which in turn is a division of Ser. No. 805,338, filed June 10, 1977, now U.S. Pat. No. 4,220,561, which in turn is a continuation in part of Ser. No. 600,275, filed July 31, 1975, and now abandoned.

SUMMARY OF THE INVENTION

The present invention relates to the use of certain heterocyclic derivatives as flavouring and odoriferous agents. The said compounds, some of which are new, have the formula (I):

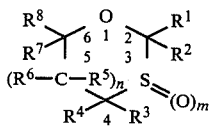

in which:
(a) m and n stand for zero or 1, and each of symbols $R^1$ to $R^8$ represents a hydrogen atom or a saturated or unsaturated, linear or branched alkyl radical containing from 1 to 11 carbon atoms, or
(b) n stands for 1 and m represents zero or 1, each of symbols $R^1$, $R^2$, $R^3$ and $R^4$ have the above described meaning, $R^5$ and $R^7$ each represents hydrogen and $R^6$ together with $R^8$ and the carbon atoms carrying them, in positions 5 and 6 respectively, form a substituted or unsubstituted cyclopentane or cyclohexane ring, or
(c) n stands for 1 and m represents zero or 1, each of symbols $R^1$, $R^3$, $R^5$, $R^6$ and $R^7$ represents hydrogen, $R^2$ represents a lower alkyl radical or a hydrogen atom, $R^4$ represents a para-substituted or unsubstituted phenyl or a substituted or unsubstituted cyclohexenyl radical, and $R^8$ stands for a lower alkyl, or
(d) n stands for 1 and m represents zero or 1, each of symbols $R^1$, $R^3$, $R^5$, $R^6$ and $R^7$ represents hydrogen, $R^2$ a p-substituted or unsubstituted phenyl or a substituted or unsubstituted cyclohexenyl radical, $R^4$ represents a lower alkyl radical or a hydrogen atom, and $R^8$ stands for a lower alkyl or a hydrogen.

As indicated hereinabove $R^1$ to $R^8$ can represent a saturated or unsaturated, linear or branched alkyl radical. Preferentially, $R^1$ to $R^8$ each represents a methyl, ethyl, propyl, butyl, sec-butyl, ter-butyl, pentyl, hexyl, heptyl or octyl radical.

In paragraphs (c) and (d) above it is indicated that $R^2$ and $R^8$ can represent a lower alkyl radical. They preferentially represent a methyl, ethyl or propyl radical.

In the above formula (I) the para-substituted phenyl groups represented by $R^4$ or $R^2$, as the case may be, include, e.g., p-methyl-phenyl, p-ethyl-phenyl, p-propyl-phenyl, p-methoxy-phenyl and p-ethoxy-phenyl. Preferred para-substituted phenyl groups are p-methyl-phenyl and p-methoxy-phenyl.

$R^4$ or $R^2$, as the case may be, can also represent a substituted or unsubstituted cyclohexenyl radical. Preferred cyclohexenyl radicals are cyclohex-3-enyl, 2,6,6-trimethyl-cyclohex-2-enyl, and 2,6,6-trimethyl-cyclohex-1-enyl. In the event that in formula (I) $R^6$ together with $R^8$ and the carbon atoms carrying them in positions 5 and 6 of the heterocyclic ring form a substituted cyclopentane or cyclohexane, the substituent can be, e.g. a lower alkyl radical such as methyl, ethyl or propyl. Methyl is a preferred substituent.

The compounds of formula (I) possess interesting organoleptic properties and accordingly, are useful as perfuming and odour-modifying agents, and as flavouring and taste-modifying agents. They can be compounded with other odoriferous substances to make perfumery compositions, in the manner conventional in the perfumery art; they can be used in combination with carriers or diluents, for perfuming a wide range of products; they can be used to modify, enhance or improve the organoleptic properties of foodstuffs, animal feeds, beverages, pharmaceutical preparations and tobacco products, and they can also be used in the manufacture of artificial flavouring compositions. Accordingly, the present invention consists in a composition comprising a compound of formula (I), as defined above, and a foodstuff, an animal feed, a beverage, a pharmaceutical preparation, a tobacco product, another odoriferous compound, or a perfume base.

This invention relates further to a method for modifying, improving or enhancing the organoleptic properties of foodstuffs, animal feeds, beverages, pharmaceutical preparations and tobacco products; as well as the odoriferous properties of perfumes and perfumed products, which method comprises adding thereto a small but effective amount of at least one compound of formula (I).

BACKGROUND OF THE INVENTION

The discovery of the utility of the compounds of formula (I) in the field of perfumery and flavours is particularly surprising. In their pure state in fact, these compounds develop a very powerful and unpleasant smell and it is only upon dilution that their odoriferous and flavouring properties become apparent.

The compounds of formula (I) belong to the class of derivatives known as 1,3-oxathianes (n=1) and 1,3-oxathiolanes (n=0). Their use, as well as that of their corresponding oxides (m=1), was hitherto unknown in perfumery and in the flavour art.

We have discovered 2-methyl-4-n-propyl-1,3-oxathiane and its corresponding oxide, viz. 2-methyl-4-n-propyl-1,3-oxathiane-3-oxide, as compounds of natural origin which can be isolated from an essential oil obtainable from the juice of the passion-fruit, *Passiflora edulis flavicarpa*. Passion-fruit juice is a commercial material available, for example, from Nationwide of Chicago, Food Brokers, Inc., 1400 Winston Plaza, Melrose Park, Ill., United States.

However, the procedure for isolating the said compounds from natural passion-fruit juice is extremely complex and uneconomical. The yield of essential oil obtained is not higher than 0.0012% by weight of the total juice treated. In order to isolate the above mentioned compounds, the juice is subjected to a preliminary distillation, by means of a special technique known as "thin layer distillation"—vide Helv. Chim. Acta, 45, 2186 (1962). This operation yield 18% by weight of an aqueous distillate from which the desired essential oil can be obtained by extraction with ethyl chloride followed by evaporation of the volatile components. The oil is then separated by column chromatography on silicic acid, by the procedure described in J. Chromatography 34, 174 (1968); and the polar fractions are then subjected to repeated separations by preparative gas chromatography to isolate the pure oxathiane derivatives.

Analytical and synthetic studies confirmed that these products were compounds of previously unknown structure.

The disadvantages and difficulties inherent in the isolation of 2-methyl-4-n-propyl-1,3-oxathiane and 2-methyl-4-n-propyl-1,3-oxathiane-3-oxide from the essential oil obtained from passion-fruit have been overcome by the discovery of a process for synthetically preparing these and the other compounds of formula (I). A particularly valuable feature of the synthetic process is that it readily yields the pure compounds, which have powerful organoleptic characteristics that are stable and perfectly reproducible; whereas, in contradistinction, the properties of the natural essential oil vary with the origin of the fruit from which it has been extracted, the method of extraction, and the purity of the essential oil recovered. Consequently, the synthetic compounds are useful as flavouring and perfuming ingredients over a wider field of application than the natural essential oil.

2-Isopropyl-1,3-oxathiolane and its phenyl analogue have been described by Kipnis et al. J.Am.Chem.Soc., 71, 3555 (1949) as liquids with fresh, aromatic aromas. In actual experience the compounds of the invention possess organoleptic properties which are by far, more superior than those described by Kipnis. The following Tables show the results of flavour evaluations carried out on 2-methyl-4-propyl-1,3-oxathiane in comparison with 2-isopropyl-1,3-oxathiolane and 2-phenyl-1,3-oxathiolane.

| | Evaluation in water | | |
|---|---|---|---|
| Ingredient | | Level | Evaluation |
| 1. | 2-Methyl-4-propyl-1,3-oxathiane (100%) | 0.1 ppm | Sweet, green, fruity typical Passion-fruit |
| 2. | 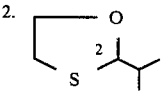 | 0.10 ppm | Strong alliaceous note, Cabbage, gas, burnt. Rotten egg. |
| 3. | 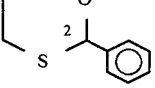 | 0.20 ppm | Weaker than 1, less fruity. Woody, floral. Slight egg character |

| | Evaluation in acidified sugar syrup* | | |
|---|---|---|---|
| Ingredient | | Level | Evaluation |
| 1. | 2-Methyl-4-propyl-1,3-oxathiane (100%) | 0.10 ppm | Fruity, juicy. Typical Passion-fruit. Blackcurrant. |
| 2. | 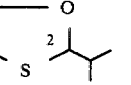 | 0.10 ppm | Lacks fruit juicy character. Burnt, gas top note. Alliaceous. |

| -continued | | | |
|---|---|---|---|
| Evaluation in acidified sugar syrup* | | | |
| Ingredient | | Level | Evaluation |
| 3. | 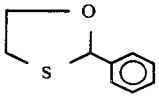 | 0.20 ppm | Less fruity than 1. Woody, floral. Vegetable character. |

*10 g of a 50% aqueous solution of citric acid in a syrup containing 600 g of sucrose per liter water.

| As reinforcer for natural Passion-fruit Juice - Comparison made with unflavoured juice. | | | |
|---|---|---|---|
| Ingredient | | Level | Evaluation |
| 1. | 2-Methyl-4-propyl-1,3-oxathiane (100%) | 0.10 ppm | Enhanced juicy character. Fresher top note. Typical. |
| 2. | 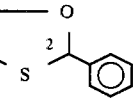 | 0.10 ppm | Burnt, alliaceous, Coffee. Not recognizable. Direction Durian. |
| 3. | 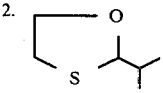 | 0.20 ppm | Green vegetable character. Cooked, fatty. Not typical. |

Concerning its olfactive properties, 2-methyl-4-propyl-1,3-oxathiane is clearly distinguishable from the above cited oxathiolane derivatives described by Kipnis. 2-Isopropyl-1,3-oxathiolane possesses an extremely powerful almost unbearable smell in its pure state. Upon dilution the same compound developed a strong odour reminiscent of rotten grass and sewage with a "carbide" by-note. 2-Phenyl-1,3-oxathiolane showed a slight spicy-green character and a vague odour reminiscent of bitter almonds with a slight rotten smell. On the contrary, 2-methyl-4-propyl-1,3-oxathiane develops in a 1% by weight solution in diethyl-phthalate a pleasant scent having a fruity-green and fresh character reminiscent of the odour developed by blackcurrent shrub leaves.

Several oxathiane and oxathiolane derivatives have been reported in the past in the scientific literature. 2-(3-Heptyl)-1,3-oxathiolane and 2-(3-amyl)-1,3-oxathiolane have been described in U.S. Pat. No. 3,025,214. Pasto et al. [J.Am.Chem.Soc., 89, 4368 (1967)] have prepared various 1,3-oxathianes which may be alkylated in the 2-position. Van Acker et al. [Tetrahedron Letters 1974, 225–8] and Stevenson [J.Am.Chem.Soc., 96, 1067 (1974)] have described 1,3-oxathiane-5-oxides and 2-t-butyl-1,3-oxathiolanes, respectively. Djerassi et al. [J.Am.Chem.Soc., 75, 3704 (1953)], Rondestvedt [J. Org. Chem. 26, 2247 (1961)], De Wolf et al. [Tetrahedron Letters, 1970 551–4], Pihlaja et al. [Acta Chem. Scand. 1970, [24], 2257] and Pasanen et al. [Acta Chem. Scand. 1971, [25] 1908] showed a variety of 1,3-oxathianes which may be substituted in the 2-and the 6-positions.

None of the above cited references describes or even suggests the possibility of using the oxathiane or oxathiolane derivatives of the present invention as flavour or perfume ingredients and, what is more, no mention appears therein of the organoleptic properties of the described compounds, most of the cited authors having in fact limited their investigations to pure theoretical physicochemical studies.

PREFERRED EMBODIMENTS OF THE INVENTION

Specific examples of the compounds defined by structural formula (I) include the following:
1. 1,3-oxathiolane
2. 2-methyl-1,3-oxathiolane
3. 5-methyl-1,3-oxathiolane
4. 2,2-dimethyl-1,3-oxathiolane
5. 2,4-dimethyl-1,3-oxathiolane
6. 2,5-dimethyl-1,3-oxathiolane
7. 2,2,4-trimethyl-1,3-oxathiolane
8. 2-pentyl-1,3-oxathiolane
9. 2-pentyl-5-methyl-1,3-oxathiolane;
10. 1,3-oxathiane
11. 2-methyl-1,3-oxathiane
12. 2,2-dimethyl-1,3-oxathiane
13. 4,4,6-trimethyl-1,3-oxathiane
14. 2,4,4,6-tetramethyl-1,3-oxathiane
15. 2-ethyl-4,4,6-trimethyl-1,3-oxathiane
16. 2-propyl-4,4,6-trimethyl-1,3-oxathiane
17. 4-propyl-1,3-oxathiane
18. 2-methyl-4-propyl-1,3-oxathiane
19. 2,2-dimethyl-4-propyl-1,3-oxathiane
20. 2-methyl-2-ethyl-4-propyl-1,3-oxathiane
21. 2-methyl-2,4-dipropyl-1,3-oxathiane
22. 2-ethyl-4-propyl-1,3-oxathiane
23. 2-ter-butyl-4-propyl-1,3-oxathiane
24. 2-pentyl-4-propyl-1,3-oxathiane
25. 2-(pent-1-enyl)-4-propyl-1,3-oxathiane
26. 2-methyl-2-hexyl-4-propyl-1,3-oxathiane
27. 2-octyl-4-propyl-1,3-oxathiane
28. 2-undecyl-4-propyl-1,3-oxathiane
29. 2-methyl-4-heptyl-1,3-oxathiane
30. 2,2-dimethyl-4-heptyl-1,3-oxathiane
31. 2-ethyl-4-heptyl-1,3-oxathiane
32. 2-pentyl-4-heptyl-1,3-oxathiane
32b. 2-methyl-6-propyl-1,3-oxathiane
32c. 2,4,4,6-tetramethyl-2-propyl-1,3-oxathiane
33. 4-(cyclohex-3-en-1-yl)-6-methyl-1,3-oxathiane
34. 2,6-dimethyl-1,4-(cyclohex-3-en-1-yl)-1,3-oxathiane;
35. 4-(2,2,6-trimethyl-cyclohex-5-en-1-yl)-6-methyl-1,3-oxathiane
36. 2,6-dimethyl-4-(2,2,6-trimethyl-cyclohex-5-en-1-yl)-1,3-oxathiane
37. 2,6-dimethyl-4-(2,2,6-trimethyl-cyclohex-6-en-1-yl)-1,3-oxathiane
38. 4-(2,2,6-trimethyl-cyclohex-6-en-1-yl)-6-methyl-1,3-oxathiane
39. 2-(2,2,6-trimethyl-cyclohex-5-en-1-yl)-4-methyl-1,3-oxathiane
40. 4-phenyl-6-methyl-1,3-oxathiane
41. 4-(p-methyl-phenyl)-6-methyl-1,3-oxathiane
42. 2,6-dimethyl-4-(p-methyl-phenyl)-1,3-oxathiane
43. 4-(p-methoxy-phenyl)-6-methyl-1,3-oxathiane
44. 2,6-dimethyl-4-(p-methoxy-phenyl)-1,3-oxathiane
45. 5-butyl-2-oxa-4-thiabicyclo[4.3.0]nonane
46. 3-methyl-5-butyl-2-oxa-4-thiabicyclo[4.3.0]nonane
47. 5,5,9-trimethyl-2-oxa-4-thiabicyclo[4.4.0]decane
48. 2,5,5,9-tetramethyl-2-oxa-4-thiabicyclo[4.4.0]decane
49. 5,5,9-trimethyl-3-ethyl-2-oxa-4-thiabicyclo[4.4.0]decane
50. 5,5,9-trimethyl-3-propyl-2-oxa-4-thiabicyclo[4.4.0]decane
51. 3,5,5,9-tetramethyl-3-propyl-2-oxa-4-thiabicyclo[4.4.0]decane
52. 1,3-Oxathiane-3-oxide
53. 2-methyl-1,3-oxathiane-3-oxide
54. 2,2-dimethyl-1,3-oxathiane-3-oxide
55. 4-propyl-1,3-oxathiane-3-oxide
56. 2-methyl-4-propyl-1,3-oxathiane-3-oxide
57. 2-pentyl-4-propyl-1,3-oxathiane-3-oxide.

In the following Table the above compounds are listed together with their physical properties. Whenever a compound is commercially available or has been previously described in the chemical literature, it will be identified by the abbreviations "c.a." (commercially available) or "p.k." (prior known), respectively. The temperatures are given in degrees centigrade and the abbreviations have the meaning common in the art.

In the above given list of compounds, whenever reference is made to alkyl substituents such as, e.g., "propyl" it is deemed to refer to the unbranched radical such as, e.g. "n-propyl".

TABLE

| Product No. | | Physical properties |
|---|---|---|
| 1. | p.k. | Suomi Kemistilehti B (1970) 43, 143 |
| 2. | p.k. | Suomi Kemistilehti B (1970) 43, 143 |
| 3. | MS: | $M^+ = 104$ (96); m/e: 89 (1), 74 (65), 60 (100), 41 (99) |
| | NMR: | 1.4 (3H, d), 2.53 (1H, d/d), 3.08 (1H, d/d), 4.02 (1H, m), 4.85 (2H, m) δ ppm |
| | IR: | 2970, 2930, 2860, 2640, 1055, 720 cm$^{-1}$ |
| 4. | p.k. | Synth. Commun. 4, 6 (1974) |
| 5. | MS: | $M^+ = 118$ (53); m/e: 103 (22), 85 (0.5), 74 (100), 59 (48), 41 (89) |
| | NMR: | 1.35 (3H, d), 1.58 (3H, d), 3.0–4.5 (3H, m), 5.25 (1H, m) δ ppm |
| 6. | p.k. | Tetrahedron 28, 3943 (1972) |
| 7. | MS: | $M^+ = 132$ (24); m/e: 117 (3), 99 (0.5), 88 (1), 74 (100), 59 (25), 43 (50), 41 (70) |
| | NMR: | 1.39 (3H, d), 1.62 (3H, s), 1.67 (3H, s), 2.76 (1H, d/d), 3.14 (1H, d/d), 4.36 (1H, m) δ ppm |
| | IR: | 2970, 2920, 2860, 2630, 1090, 590 cm$^{-1}$ |
| 8. | MS: | $M^+ = 160$ (7); m/e: 89 (100), 60 (48), 61 (45), 45 (9) |
| | NMR: | 0.88 (3H, t), 3.0 (2H, d/d), 3.76 (1H, d/d/d), 4.35 1H, d/t), 5.08 (1H, t) δ ppm |
| | IR: | 2955, 2925, 2855, 2720, 1070, 658 cm$^{-1}$ |
| 9. | MS: | $M^+ = 174$ (8.5); m/e: 127 (2), 115 ( ), 103 (100), 83 (2), 74 (72), 55 (64), 41 (62). |
| | NMR: | 0.90 (3H, t), 1.40 (3H, d), 2.61 (1H, d/d), 3.09 (1H, d/d), 4.18 (1H, m), 5.15 (1H, t) δ ppm |
| | IR: | 2950, 2915, 2850, 2620, 1090, 655 cm$^{-1}$ |
| 10. | p.k. | Acta Chem. Scand. 24, 2257 (1970) |
| 11. | p.k. | Acta Chem. Scand. 24, 2257 (1970) |
| 12. | p.k. | Acta Chem. Scand. 24, 2257 (1970) |
| 13. | B.p. | 61°/11 Torr |
| | MS: | $M^+ = 146$ (62), 131 (7.6), 113 (0.9), 102 (20.5), 87 (35.3), 83 (16.1), 74 (31.7), 69 (10.7), 67 (7.6), 59 (48.7), 56 (61.2), 43 (100), 41 (50.4) |
| | NMR: | (60 MHz; CDCl$_3$): 1.12–1.63 (5H, m), 1.26 (6H, s), 3.40–3.92 (1H, sext.), 4.63–5.10 (2H, d of d) δ ppm |
| 14. | B.p. | 65°/15 Torr |
| | MS: | $M^+ = 160$ (45.8), 145 (29.5), 132 (1.0), 116 (18.9), 101 (41.5), 88 (12.1), 83 (42.1), 74 (72.1), 69 (10.5), 67 (9.7), 61 (53.7), 60 (100), 59 (69.4), 55 (34.2), 43 (32.1), 41 (45.8) |
| | NMR | (60 MHz; CDCl$_3$): 1.23 (6H, s); 1.15–1.55 (8H, m), 3.47–4.06 (1H, sext.), 4.78–5.15 (1H, q) δ ppm |
| 15. | B.p. | 77°/13 Torr |
| | MS: | $M^+ = 174$ (19.8), 145 (100), 116 (3.4), 101 (29.7), 83 (84.5), 74 (80.7), 69 (12.6), 67 (8.2), 61 (42.5), 60 (62.3), 59 (63.8), 55 (37.2), 43 (22.7), 41 (58.4) |
| | NMR | (60 MHz; CDCl$_3$): 0.85–1.10 (3H, t), 1.25 (6H, s), 1.12–1.95 (7H, m), 3.42–4.02 (1H, sext.), 4.67–4.87 (1H, t) δ ppm |
| 16. | B.p. | 95°/13 Torr |
| | MS: | $M^+ = 188$ (13.2), 145 (100), 116 (3.9), 101 (27.8), 88 (12.8), 83 (76.7), 74 (50.7), 69 (11.4), 67 (6.4), |

TABLE-continued

| Product No. | | Physical properties |
|---|---|---|
| | | 61 (39.7), 60 (58.4), 59 (40.2), 55 (44.3), 43 (13.2), 41 (41.5) |
| | NMR | (60 MHz; CDCl$_3$): 0.8–1.05 (3H, t), 1.25 (6H, s), 1.15–1.90 (9H, m), 3.40–4.02 (1H, sext.), 4.70–4.97 (1H, t) δ ppm |
| 17. | MS: | M$^+$ = 146 (50); m/e: 114 (27), 103 (95), 73 (100), 55 (57), 45 (49) |
| | NMR: | 0.92 (3H, t), — 1.80 (2H, d/d), 3.02 (1H, bm), 3.52 (1H, m), 4.15 (1H, d/tr), 4.80 (2H, s) δ ppm |
| | IR: | 2950, 2920, 2860, 2720, 1085, 575 cm$^{-1}$ |
| 18. | vide | p. 28 & 29 of this specification |
| 19. | MS: | M$^+$ = 174 (37); m/e: 159 (35), 116 (49), 101 (70), 87 (100), 73 (55), 55 (98), 41 (76) |
| | NMR: | 0.90 (3H, tr), 1.47 (3H, s), 1.64 (3H, s), 3.12 (1H, bm), 3.87 (2H, d/d) δ ppm |
| | IR: | 2960, 2925, 2870, 2720, 1080, 600 cm$^{-1}$ |
| 20. | MS: | M$^+$ = 188 (3.5); m/e: 173 (6), 159 (100), 116 (19), 101 (41), 83 (66), 73 (57), 55 (87), 43 (75) |
| | NMR: | 0.95 (6H, m), 1.4 (6H, m), 1.6 (3H, s), 3.09 (1H, bm), 4.85 (2H, m) δ ppm |
| | IR: | 2960, 2920, 2865, 2720, 1080, 585 cm$^{-1}$ |
| 22. | MS: | M$^+$ = 174 (13); m/e: 145 (100), 101 (8.5), 83 (24), 73 (21), 55 (48), 41 (32) |
| | NMR: | 0.99 (6H, m), — 2.99 (1H, bm), 3.65 (1H, m), 4.22 (1H, d/tr), 4.64 (1H, tr) δ ppm |
| | IR: | 2960, 2920, 2870, 2840, 2730, 1100, 1075, 575 cm$^{-1}$ |
| 23. | MS: | M$^+$ = 202 (2); m/e: 146 (100), 83 (27), 73 (5), 55 (35), 41 (20) |
| | NMR: | 1.0 (12H, bs), 1.4–1.9 (6H, m), 2.98 (1H, bm), 3.65 (1H, m), 4.25 (1H, d/tr), 4.45 (1H, s) δ ppm |
| | IR: | 2950, 2920, 2855, 2720, 1085, 640 cm$^{-1}$ |
| 24. | MS: | M$^+$ = 216 (4); m/e: 145 (100), 117 (3), 101 (8), 83 (28), 73 (13), 55 (42), 41 (26) |
| | NMR: | 0.89 (6H, bm), 3.0 (1b, bm), 3.62 (1H, m), 4.2 (1H, d/t), 4.7 (1H, t) δ ppm |
| | IR: | 2955, 2920, 2850, 2725, 1085, 660 cm$^{-1}$ |
| 25. | MS: | M$^+$ = 214 (31); m/e: 185 (6), 171 (18.5), 145 (5.5), 131 (2), 116 (22), 98 (60), 87 (70), 73 (47), 55 (100), 41 (88). |
| | IR: | 3040, 3015, 2960, 2880, 1665, 1075, 960 720 cm$^{-1}$ |
| 26. | MS: | M$^+$ = 244 (0.5); m/e: 229 (1), 159 (42), 128 (4), 116 (23.5), 101 (20), 87 (32), 73 (20), 58 (65), 43 (100), 41 (46) |
| | NMR: | 0.9 (6H, bm), 1.6 (3H, s), 3.16 (1H, bm), 3.89 (2H, m) δ ppm |
| | IR: | 2940, 2910, 2850, 2720, 1085, 600 cm$^{-1}$ |
| 27. | MS: | M$^+$ = 258 (2); m/e: 145 (100), 124 (2.5), 117 (4), 101 (5), 87 (11), 83 (25), 69 (9.5), 55 (39), 41 (29), 29 (92) |
| | NMR: | 0.89 (6H, bm), 2.98 (1H, bm), 3.63 (1H, m), 4.2 (1H, d, t), 4.7 (1H, t) δ ppm |
| | IR: | 2950, 2915, 2845, 2720, 1085, 660 cm$^{-1}$ |
| 28. | MS: | M$^+$ = 300 (—); m/e: 166 (2), 145 (100), 116 (5.5), 101 (5.5), 83 (22), 69 (8.5), 55 (35), 41 (25) |
| | NMR: | 0.91 (6H, bm), 2.97 (1H, bm), 3.7 (1H, m), 4.19 (1H, d/t), 4.69 (1H, t) δ ppm |
| | IR: | 2940, 2910, 2835, 2720, 1095, 1075, 660 cm$^{-1}$ |
| 29. | MS: | M$^+$ = 216 (43); m/e: 201 (57), 170 (78), 157 (2.5), 143 (37), 129 (18), 115 (61), 101 (54), 87 (85), 73 (65), 55 (100), 41 (80) |
| | NMR: | 0.89 (3H, t), 1.48 (3H, d), 1.7 (2H, m), 3.01 (1H, bm), 3.56 (1H, m), 4.2 (1H, d/t), 4.81 (1H, q) δ ppm |
| | IR: | 2950, 2920, 2850, 2720, 1095, 670 cm$^{-1}$ |
| 30. | MS: | M$^+$ = 230 (4); m/e: 215 (8), 199 (—), 187 (0.5), 172 (14), 157 (—), 143 (36), 129 (21), 115 (53), 101 (47), 87 (87), 64 (45), 55 (80), 43 (100) |
| | NMR: | 0.90 (3H, t), 1.52 (3H, s), 1.69 (3H, s), 3.12 (1H, bm), 3.92 (2H, m) δ ppm |
| | IR: | 2950, 2920, 2850, 2720, 1080, 595 cm$^{-1}$ |
| 31. | MS: | M$^+$ = 230 (6.5); m/e: 216, (—), 201 (100), 185 (0.5), 170 (3), 157 (0.5), 143 (2), 129 (1), 115 (6.5), 97 (13), 83 (33), 69 (33), 55 (48), 41 (42) |
| | NMR: | 0.99 (6H, m), 2.95 (1H, bm), 3.60 (1H, m), 4.18 (1H, d/d), 4.61 (1H, t) δ ppm |
| | IR: | 2955, 2920, 2850, 2725, 1105, 1090, 720 cm$^{-1}$ |
| 32. | MS: | M$^+$ = 272 (2); m/e: 201 (100), 182 (0.5), 170 (3), 157 (0.5), 143 (5.5), 129 (4), 115 (11), 97 (11), 83 (33), 69 (31), 55 (55), 41 (52) |
| | NMR: | 0.87 (6H, bt), 2.97 (1H, bm), 3.6 (1H, m), 4.16 (1H, d/tr), 4.65 (1H, t) δ ppm |
| | IR: | 2950, 2920, 2850, 2720, 1090, 720 cm$^{-1}$ |
| 32b. | B.p. | 75°/9 Torr |
| | NMR: | 0.92 (34.6), 1.46 (3H, d, J=6Hz), 1.2–1.9 (6H, m), 2.5–3.2 (1H, m), 3.2–3.7 (1H, m), 4.89 (1H, q, J=6Hz) δ ppm |
| | MS: | M$^+$ = 160 (34), 87 (100), 41 (51), 60 (43), 67 (38), 80 (36.5), 55 (35.5), 45 (33), 101 (21.5), 116 (21) |
| 32c. | B.p. | 89°/11 Torr |
| | MS: | 202 (1.7), 187 (3.3), 159 (77.6), 116 (36.0), 101 (54.2), 87 (22.9), 83 (72.0), 74 (80.4), 69 (20.6), 67 (10.3), 61 (66.8), 60 (94.4), 59 (64.9), 55 (38.3), 43 (100), 41 (26.2) |
| | NMR | (90 MHz; CDCl$_3$) 0.80–1.06 (3H, t), 1.25 (6H, s), 1.15–1.90 (12H, m), 3.70–4.25 (1H, m) δ ppm |
| 33. | B.p. | 73°/0.001 Torr |
| | MS: | M$^+$ = 198 (10.5), 117 (100), 73 (81), 79 (50), 93 (34), 45 (31.5), 41 (26.5), 87 (23), 53 (14), 67 (12), |
| | NMR: | 1.2 (3H, d, J=6Hz), 1.4–2.4 (9H, m), 2.5–4.0 (2H, m), 4.87 (2H, s), 5.7 (2H, bs) δ ppm |
| 34. | B.p. | 78°/0.001 Torr |
| | MS: | M$^+$ = 212 (14), 79 (100), 93 (92), 80 (84), 87 (80), 131 (76), 92 (66), 91 (55), 45 (52), 41 (47) |
| | NMR: | 1.16 (1H, d), 1.22 (2H, d), 1.39 (1H, d), 1.46 (2H, d), 1.6–2.5 (9H, m), 2.7–4.0 (2H, m), 4.7–5.3 (1H, m), 5.7 (2H, s) δ ppm |
| 35. | Isomer A - B.p. 100°/0.5 Torr | |
| | MS: | M$^+$ = 240 (3.5), 73 (100), 117 (61), 87 (12), 41 (12), 55 (5.7). |
| | NMR: | 0.88 (3H, s), 1.08 (3H, s), 1.3 (3H, d, J=6Hz), 1.82 (3H, m), 3.55 (1H, m), 4.25 (1H, bm), 4.54 (1H, d, J=11 Hz), 5.19 (1H, d, J=11Hz), 5.45 (1H, m) δ ppm |
| | Isomer B - B.p. 100°/0.5 Torr | |
| | MS: | M$^+$ = 240 (4), 73 (100), 117 (65), 41 (10.7), 87 (10.4), 55 (5.5) |
| | NMR: | 0.9 (3H, s), 1.09 (3H, s). 1.18 (3H, d, J=6Hz), 1.8 (3H, m), 3.1–3.8 (2H, m), 4.87 (2H, s), 5.5 (1H, m) δ ppm |
| 36. | B.P. | 100°/0,5 Torr |
| | MS: | M$^+$ = 254 (2), 87 (100), 131 (34), 45 (10), 41 (9), 123 (4.6), 107 (4.4), 55 (4.1) |
| | NMR: | 0.88 (3H, s), 1.07 (3H, s), 1.2 (3H, d, J=6Hz), 1.45 (3H, d, J=6Hz), 1.8 (3H, m), 3.1–3.8 (2H, m), 4.85 (1H, q, J=6Hz) δ ppm |
| 37. | B.p. | 85°/0.05 Torr |
| | MS: | M$^+$ = 254 (35), 41 (100), 135 (85), 107 (76), 43 (71), 55 (71), 61 (71), 93 (69), 161 (67), 91 (62), 119 (62), 121 (62), 69 (59), 167 (59), 79 (47) |
| | NMR: | 0.99 (3H, s), 1.09 (3H, s), 1.24 (3H, d, J=6Hz), 1.45 and 1.5 (3H, d, d, J=6Hz), 1.88 (3H, s), 3.3–4.2 (2H, m), 4.6–5.4 (1H, m) δ ppm |
| 38. | Isomer A - B.p. 95°/0.2 Torr | |
| | MS: | M$^+$ = 240 (45.5), 135 (100), 43 (93), 91 (82), 149 (75), 41 (72), 93 (70), 107 (61), 45 (47.5), 55 (46.5), 69 (43), 79 (41), 81 (38.5), 121 (37.5) |
| | NMR: | 1.0 (3H, s), 1.09 (3H, s), 1.2 (3H, d, J=6Hz), 1.88 (3H, s), 3.3–3.8 (2H, m), 4.87 (2H, s) δ ppm |
| | Isomer B - B.p. 95°/0.2 Torr | |
| | MS: | M$^+$ = 240 (33), 43 (100), 135 (98), 93 (80), 41 (77), 95 (69), 149 (65), 107 (64), 121 (51), 55 (49), 69 (43.5), 79 (42) |
| | NMR: | 1.0 (3H, s), 1.12 (3H, s), 1.4 (3H, d, J=6Hz), 1.92 (3H, s), 2.4–3.0 (1H, m), 3.8–4.4 (1H, m), 4.6 (1H, d, J=11Hz), 5.23 (1H, d, J=1Hz) δ ppm |
| 39. | Isomer A - B.p. 110°/0.1 Torr | |
| | MS: | M$^+$ = 240 (4.7), 75 (100), 117 (85), 123 (76), 41 (69), 81 (50), 107 (40), 43 (39.5), 93 (36.5), 45 (36.5), 55 (35), 69 (33) |
| | NMR: | 0.87 (3H, s), 0.95 (3H, s), 1.23 (3H, d, J=6Hz), 1.81 (3H, s), 2.5–3.9 (2H, m), 4.86 (2H, d, J=2Hz), 5.53 (1H, m) δ ppm |
| | Isomer B - B.p. 110°/0.1 Torr | |
| | MS: | M$^+$ = 240 (4.3), 75 (100), 117 (79), 123 (71), 41 (38), 81 (38), 43 (28), 210 (19), 107 (18.5) |

TABLE-continued

| Product No. | | Physical properties |
|---|---|---|
| | NMR: | 0.9 (3H, s), 1.0 (3H, s), 1.24 (3H, d, J=6Hz), 1.8 (3H, m), 2.5-3.7 (2H, m), 4.86 (2H, s), 5.5 (1H, m) δ ppm |
| 40. | B.p. | 80°/0.1 Torr |
| | MS: | M+ = 194 (31), 104 (100), 43 (51), 121 (43), 122 (42), 91 (26), 161 (21), 77 (21), 45 (18) |
| | NMR: | 1.23 (1.3H, D, J=6Hz), 1.24 (1.7H, d, J=6Hz), 1.7-2.3 (2H, m), 3.2-4.4 (2H, m), 4.87 (0.8H, s), 4.93 (1.2H, s), 7.29 (5H, m) δ ppm |
| 41. | B.p. | 140°/0.01 Torr |
| | MS: | M+ = 208 (37), 118 (100), 43 (60), 117 (39), 135 (37), 136 (35), 105 (35), 91 (34) |
| | NMR: | 1.25 (3H, d, J=6Hz), 2.32 (3H, s), 3.3-4.5 (2H, m), 4.9 (0.7H, s), 4.98 (1.3H, s), 7.22 (4H, m) δ ppm |
| 42. | B.p. | 100°/0.001 Torr |
| | MS: | M+ = 222 (40), 136 (100), 135 (58), 118 (55), 145 (38), 91 (34), 163 (31.5), 105 (26), 43 (24) |
| | NMR: | 1.15 (3H, d, J=6Hz), 1.45 (3H, d, J=6Hz), 2.31 (3H, s), 3.7 (1H, m), 4.22 (1H, m), 5.0 (1H, m) δ ppm |
| 43. | B.p. | 100°/0.01 Torr |
| | MS: | M+ = 224 (50), 134 (100), 135 (98), 121 (94), 136 (78), 43 (72), 147 (46), 91 (39), 77 (39), 45 (35) |
| | NMR: | 1.25 (3H, d, J=6Hz), 1.5-2.0 (2H, m), 3.3-4.3 (2H, m), 3.77 (3H, s), 4.96 (2H, s), 6.8-7.4 (4H, m) δ ppm |
| 44. | B.p. | 110°/0.01 Torr |
| | MS: | M+ = 238 (47), 152 (100), 161 (75), 134 (62), 43 (33), 121 (31), 91 (28), 204 (17), 65 (16), 77 (16) |
| | NMR: | 1.16 (3H, d, J=6Hz), 1.3-1.6 (3H, m), 3.5-4.0 (1H m), 3.79 (1H, s), 3.8 (2H, s), 4.27 (1H, t), 4.8-5.3 (1H, m), 6.8-7.6 (4H, m) δ ppm |
| 45. | B.p. | 73°/0.01 Torr |
| | MS: | M+ = 200 (42), 67 (100), 41 (97), 168 (62), 110 (60), 81 (60), 55 (56), 95 (47), 143 (36) |
| | NMR: | 0.9 (3H, t), 1.2-2.1 (13H, m), 3.4 (1H, m), 3.83 (1H, s), 4.72 (1.6H, s), 4.9 (0.4H, s) δ ppm |
| 46. | B.p. | 66°/0.01 Torr |
| | MS: | M+ = 214 (43), 67 (100), 95 (86), 81 (81), 41 (79), 101 (58), 60 (57), 168 (43), 114 (40), 55 (38), 87 (37) |
| | NMR: | 0.1 (3H, t), 1.43 (3H, d), 3.4 (1H, bm), 3.9 (1H, bs), 4.25 (1H, q) δ ppm |
| 47. | B.p. | 118°/12 Torr |
| | MS: | M+ = 200 (74.3), 185 (19.6), 167 (2.3), 154 (23.7), 139 (20.5), 137 (19.6), 136 (15.6), 121 (31.8), 112 (29.1), 111 (28.6), 110 (22.3), 109 (33.2), 95 (59.1), 81 (77.3), 75 (100), 74 (59.5), 69 (73.6), 67 (32.7), 59 (29.5), 55 (55.9), 53 (21.8), 43 (30.0), 41 (89.8) |
| | NMR: | 0.70-1.08 (5H, m), 1.10-1.32 (4H, s), 1.40-2.15 (8H, m), 3.83-4.05 (1H, m), 4.60-5.17 (2H, q) δ ppm |
| 48. | B.p. | 113°/13 Torr |
| | MS: | M+ = 214 (59.4), 199 (48.9), 170 (52.8), 155 (24.4), 137 (81.1), 128 (43.3), 127 (41.67), 117 (26.7), 109 (20.6), 95 (100), 81 (99.3), 75 (89.4), 74 (62.8), 69 (55.0), 67 (40.0), 59 (40.6), 55 (62.2), 41 (98.9) |
| | NMR: | 0.75-1.25 (12H, m), 1.40-2.10 (8H, m), 3.86-4.08 (1H, m), 4.80-5.18 (1H, q) δ ppm |
| 49. | B.p. | 110°/13 Torr |
| | MS: | M+ = 228 (10.7), 199 (67.6), 170 (7.1), 155 (6.9), 137 (100), 128 (14.8), 127 (15.3), 121 (14.3), 109 (9.3), 95 (54.9), 81 (62.6), 75 (31.9), 74 (26.6), 69 (26.9), 67 (23.1), 59 (15.4), 55 (34.6), 41 (59.9) |
| | NMR: | 0.7-1.20 (12H, m), 1.50-2.10 (10H, m), 3.85-4.05 (1H, m), 4.70-4.85 (1H, t) δ ppm |
| 50. | B.p. | 56°/0.15 Torr |
| | MS: | M+ = 242 (7.4), 199 (67.3), 170 (6.9), 155 (6.5), 152 (4.1), 137 (100), 128 (13.8), 127 (14.3), 121 (9.2), 109 (8.8), 95 (44.2), 81 (53.5), 75 (27.6), 74 (19.8), 69 (22.1), 67 (19.4), 59 (12.4), 55 (34.1), 43 (18.0), 41 (43.8) |
| | NMR: | 0.70-1.25 (12H, m), 1.39-2.15 (12H, m), 3.85-4.05 (1H, m), 4.75-5.05 (1H, t) δ ppm |
| 51. | B.p. | 146°/14 Torr |
| | MS: | M+ = 256 (0.9), 241 (6.5), 213 (43.3), 170 (36.8), 155 (9.5), 137 (83.6), 128 (23.9), 127 (23.6), 109 (19.9), 95 (88.6), 81 (82.1), 75 (32.8), 74 (26.9), 69 (34.3), 67 (44.8), 59 (18.9), 55 (44.8), 53 (20.9), 43 (100), 41 (76.1) |
| | NMR: | 0.75-1.24 (12H, m), 1.40-2.05 (15H, m), 4-4.30 (1H, m) δ ppm |
| 52. | MS: | M+ = 120 (<1); m/e: 90 (76), 73 (17), 42 (29), 41 (100) |
| | NMR: | 1.45-3.55 (4H, bm), 3.83 (2H, t), 4.42 (1H, d, d), 4.80 (1H, d, d) δ ppm |
| | IR: | 2960, 2910, 2850, 2730, 1095, 1050, 830 cm$^{-1}$ |
| 53. | MS: | M+ = 134 (<1); m/e: 90 (86), 73 (22), 45 (24), 43 (37), 41 (100) |
| | IR: | 2960, 2910, 2860, 2725, 1110, 1045, 865, 835 cm$^{-1}$ |
| 54. | MS: | M+ = 148 (7); m/e: 130 (26), 90 (100), 73 (29), 61 (44), 59 (46), 43 (94), 41 (86) |
| | IR: | 2980, 2925, 2870, 2720, 1080, 1060, 1040, 855 cm$^{-1}$ |
| 55. | MS: | M+ = 162 (<1); m/e: 132 (53), 89 (46), 83 (38), 77 (24), 55 (100), 41 (47) |
| | IR: | 2950, 2925, 2870, 2725, 1105, 1045, 860 cm$^{-1}$ |
| 56. | vide | p. 31 of this specification |
| 57. | MS: | M+ = 232 (0); m/e: 145 (100), 87 (18), 83 (42), 67 (17), 55 (69), 45 (18), 43 (23), 41 (53) |

Depending upon the nature of the other constituents in compositions to which they are added, the compounds of formula (I) can develop various odoriferous or gustative notes such as fruity, green, alliaceous, caramel-like or slightly burnt and rubbery notes.

These organoleptic characteristics render the compounds of formula (I) particularly suitable for the aromatization of beverages such as fruit juices, syrups, vegetable juices or coffee drinks and soups or for the aromatization of tobacco products.

When the compounds of formula (I) are used as perfuming ingredients, they can develop upon dilution powerful and natural fruity type fragrances.

The term "foodstuff" is used broadly and includes, for example, coffee, tea or chocolate. The term "tobacco" includes natural tobacco and tobacco substitutes, whether of natural or synthetic origin, intended for smoking in pipes, cigars or cigarettes, for chewing, or for use as snuff.

The concentration at which the compounds of formula (I) can be used as flavouring agents, in accordance with the invention, can vary widely, depending upon the specific organoleptic effect desired and the type of material to which they are added. Typically, interesting flavouring effects can be achieved with amounts ranging from 0.01 to 100 ppm (parts per million) by weight of the flavoured material.

Preferentially, this concentration is comprised between about 0.01 and 10 ppm. The compounds of formula (I) in which m is 1, viz. the oxide derivatives, can be used at concentrations of about 0.1-50 ppm. The effects achieved by the use of these oxides is particularly interesting as they enhance the natural character of the fruity note of the materials to which they are added. Their effect, though, is less markedly characteristic than that achieved by the corresponding oxathianes or oxathiolanes compounds; specifically, they are less powerful than these compounds.

When used as perfuming ingredients, the compounds of formula (I) can be used at concentrations which typically are on the order of 0.01% by weight based on the total weight of the perfuming composition in which they are incorporated. Preferential concentrations range from about 0.01 to 0.1 %. The compounds of formula (I) can be used alone or in compositions containing one or more other flavouring or odoriferous componds, in diluted or concentrated solutions in solvents conventionally employed for flavouring and perfumery, for example ethyl alcohol, triacetin, diethyleneglycol and diethyl phthalate.

Among the compounds listed above, the following possess especially interesting organoleptic properties:
2-methyl-4-propyl-1,3-oxathiane,
4-propyl-1,3-oxathiane,
2,2-dimethyl-4-propyl-1,3-oxathiane,
2-ethyl-4-propyl-1,3-oxathiane,
2-pentyl-4-propyl-1,3-oxathiane,
4-(2,2,6-trimethyl-cyclohex-5-en-1-yl)-6-methyl-1,3-oxathiane
and 5-butyl-2-oxa-4-thiabicyclo[4.3.0.]nonane, together with their corresponding 3-oxide derivatives, namely the 2-methyl-4-propyl-1,3-oxathiane-3-oxide.

The compounds of formula (I), in which m is zero, can be obtained by a process which comprises reacting a thiol-alcohol of formula (II):

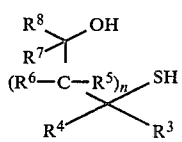

(in which symbols $R^3$ to $R^8$ and index n have the aforementioned meaning) with a carbonyl compound of formula (III):

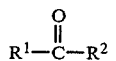

(in which $R^1$ and $R^2$ have the meaning described above) in the presence of an acid catalyst.

The sulphur compounds of formula (II), used as starting materials in the process described above, can be obtained by a process which consists (a) in reacting hydrogen sulphide and the desired unsaturated carboxylic acid or, if desired, one of its corresponding esters and (b) reducing or hydrolizing, respectively, the sulphur addition compound thus obtained.

The alcohols of formula (II) can also be prepared by reducing the corresponding aldehydes, e.g. according to the procedure described in German Patent Application DOS No. 2,338,680.

In the preparation of the compounds of formula (I), carbonyl derivatives (III) can be replaced by their corresponding ketal or acetal derivatives.

Typically, the compounds of formula (I) were prepared in accordance with the following method:

A mixture of 1.34 g (10 mM) of 3-mercapto-hexanol, 2.2 g (50 mM) of acetaldehyde and 20 ml of cyclohexane were refluxed in the presence of a few milligrams of p-toluenesulphonic acid in a reaction vessel equipped with a water separator device. The reaction was over in about 30 minutes as indicated by the total recovery of the theoretical amount of water formed. The residue was successively washed with a 10% aqueous $NaHCO_3$ solution and water. The aqueous phase was extracted with ether (2 fractions) and the ethereal layers thus separated were concentrated to yield 1.5 g of a residue which on distillation gave a fraction having b.p. 82°-5°/10 Torr; $n_D=1.4790$; $d_4^{20}=0.9703$.

IR (neat): 2940, 2905, 2804, 2700, 1083, 664 $cm^{-1}$.

NMR ($CDCl_3$; 90 MHz): 0.95 (3H); 1.5 (3H, d); 1.5 (6H, m); 3.08 (1H, m); 3.58 and 4.20 (2H, m); 4.8 (1H, q) δ ppm.

The material obtained essentially consisted of a mixture of two stereoisomers, defined as cis and trans, in a weight ratio of about 9:1, respectively. Consequently, 2-methyl-4-propyl-1,3-oxathiane is better represented by the following formula:

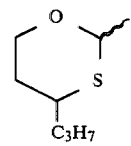

which in turn indifferently defines one or the other of the compounds of formula:

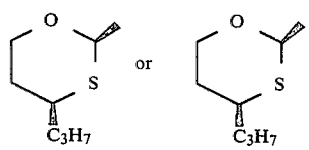

Moreover, each of the above indicated epimers can occur in a racemic form or in the form of one of its enantiomers. This applies equally well to all the compounds of formula (I).

These isomers could be separated by means of vapour phase chromatography by using a 20 M CARBOWAX column. The compounds obtained were characterized by the following physical data:

Isomer A

MS: $M^+=160$ (64.5); $M+2^+$ (2.5); m/e: 145 (67.5); 116 (13); 101 (51); 87 (82.5); 73 (71.5); 60 (58); 55 (100); 45 (72); 41 (72); 41 (66.5).

Isomer B

MS: $M^+=160$ (62); $M+2^+$ (2.5); m/e: 145 (65); 116 (12.5); 101 (48); 87 (78.5); 73 (75); 60 (62.5); 55 (100); 45 (78); 41 (62).

For all practical purposes and in accordance with the invention, the mixture obtained in accordance with the above described method can satisfactorily be employed. However, especially for their use in perfumery, the two isomers can be separated and individually used for perfume compounding, the cis isomer being preferred.

3-Mercapto-hexanol, used as starting material in the above described process, can be synthetized according to the procedure described in Houben-Weyl, Methoden der Organischen Chemie 9, 21 (1955), or in Acta Chem. Scand. 25, 1908 (1971). This alcohol had the following analytical data:

B.p. 45°/0.001 Torr; $n_D=1.4796$; $d_4^{20}=0.9744$.

Typically, the alcohol is prepared as follows:
(a) 8.36 g (0.11 M) of thio-acetic acid were added dropwise to 9.8 g (0.1 M) of hex-1-en-3-one while the reaction temperature increased to 50°. After 1 h stirring at that temperature, 3-oxo-hexyl thioacetate was recovered at b.p. 111°-3°/10 Torr.
(b) 15.6 g (0.09 M) of the said thioacetate in 50 ml of anhydrous ether was added slowly to a suspension of 3.8 g (0.1 M) of $LiAlH_4$ in 100 ml ether in a nitrogen atmosphere. Once the addition was over, the reaction mixture was refluxed during 1 h, then it was cooled to 0° and the excess of LiAlH₄ was decomposed by slow addition of 10 ml of water followed by 200 ml of 10% HCl. After separation, the ethereal phase was washed with water, dried over MgSO₄ and concentrated. A distillation over a Vigreux column afforded the desired thio-alcohol in 85% yield.

Alternatively, the alcohols of formula (II) can be synthesized by reacting an α,β-unsaturated ketone with thio-acetic acid as follows:

(a') 0.11 M of thio-acetic acid were added dropwise to 0.1 M of the α,β-unsaturated ketone of formula

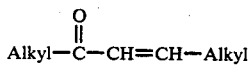

The reaction mixture was then heated for a time period ranging from about 1 to 6 h at a temperature of about 50°–105°.

(b') The reduction of the obtained thio-acetate into its corresponding thio-alcohol was carried out by means of LiAlH₄ as indicated sub letter (b).

The compounds of formula (I) in which index m is 1, can be prepared by oxidizing the oxathianes or oxathiolanes of formula (I), in which m is zero, by conventional techniques. Thus 2-methyl-4-propyl-1,3-oxathiane-3-oxide, e.g., was prepared by oxidizing 2-methyl-4-propyl-1,3-oxathiane by means of $H_2O_2$ according to the procedure described in J. Am. Chem. Soc. 90, 309 (1968) or by means of perbenzoic acid, m-chloro-perbenzoic acid-vide: Houben-Weyl, IX, Georg Thieme Verlag, 213 (1955)-, or m-periodic acid-vide; J. Org. Chem. 27, 282 (1962)-.

Typically, 2-methyl-4-propyl-1,3-oxathiane-3-oxide could be prepared as follows:

40 mMoles of 2-methyl-4-propyl-1,3-oxathiane were dissolved in 20 ml of $CH_2Cl_2$ and to this solution there were added 38 mMoles of m-chloro-perbenzoic acid (80%) in 60 ml of $CH_2Cl_2$, and the reaction mixture was stirred at 0° during 1 h. The formed acid was precipitated by the addition of gaseous $NH_3$. After filtration, and evaporation of the volatile fractions, the crude material was fractionally distilled under vacuum, and the distillate subjected to separation by column chromatography on $SiO_2$ (Merck 60; C), eluant: $CHCl_3$.

The isolated compound had the following physical data:

electronic ionization: m/e: 132 (41.8); 89 (42.5); 83 (41.4); 77 (23.1); 55 (100); 43 (16.7); 41 (38.6); 29 (19.2); 27 (18.4);

chemical ionization: $(M+1)^+ = 177$ (23); m/e: 161 (28); 145 (17); 133 (100); 117 (99); 115 (46.5); 99 (14.5); 83 (50.5);

IR: 2710, 1035 cm$^{-1}$;

NMR: (90 MHz; CDCl₃): 0.97 (3H, t); 1.68 (3H, d); 1.1 to 2.2 (6H, m); 2.67 (1H, broad band m); 3.62 (1H, m); 4.02 (1H, m); 4.1 (1H, q) δ ppm.

Due to the presence of an oxygen atom bonded to the cyclanic sulphur and the simultaneous presence of chirality centres in positions 2 and 4 of the ring, 2-methyl-4-propyl-1,3-oxathiane-3-oxide can occur not only in the form of a cis or trans cyclanic isomer relative to the substituents on the ring, but also as an axial or an equatorial isomer with regard to its sulphoxide bond.

The separation of these four isomers could be achieved as indicated above by careful fractional distillation followed by column chromatography on silica gel (eluant: CHCl₃). The isolated compounds showed the following analytical characteristics:

cis-equatorial: MS: M⁺ = 160 (<1); m/e: 132 (52), 89 (52), 83 (40), 77 (23), 55 (100), 43 (68), 41 (53), 29 (65) IR (neat): 2960, 2920, 2860, 1460, 1100 cm⁻¹;

cis-axial: MS: M⁺ = 160 (<1); m/e: 132 (64), 89 (62), 83 (49), 77 (28), 55 (100), 41 (46). IR (KBr): 2950, 2850, 1450, 1100 cm⁻¹;

trans-equatorial: MS: M⁺ = 160 (<1); m/e: 132 (61), 89 (58), 83 (45), 77 (39), 55 (100), 41 (51). IR (neat): 2960, 2920, 2860, 1460, 1100, 1050 cm⁻¹;

trans-axial: MS: M⁺ = 160 (<1); m/e: 132 (25), 89 (25), 83 (34), 55 (100), 43 (38), 41 (53). IR (neat): 2960, 2920, 2860, 1450, 1100, 1040 cm⁻¹.

The above described processes have been used for the preparation of the compounds listed in the Table. The temperatures are indicated in degrees centigrade and the abbreviations have the meaning common in the art.

The invention is illustrated by the following Examples.

EXAMPLE 1

Aromatization of foodstuffs

A.

Two syrups of raspberry and black-currant type, respectively, were prepared by diluting 1 part by weight of commercial syrup with 4 and 9 parts by weight, respectively, of water. The beverages thus obtained were flavoured with a proportion of 0.50 ppm and 0.10 ppm, respectively, of 2-methyl-4-propyl-1,3-oxathiane.

The flavoured beverages were subjected to organoleptic evaluation by a panel of experienced tasters whose judgment was expressed as follows:

the flavoured raspberry syrup possessed an improved top note and an overall aroma which was fuller and fresher than that of the unflavoured syrup, the flavoured black-currant syrup showed a fuller and a more natural taste than the unflavoured one. It possessed moreover a better defined green and woody note.

B.

A commercially available tomato juice possessing a bland taste was flavoured with 2-methyl-4-propyl-1,3-oxathiane by using it at a concentration of 0.10 ppm based on the total weight of the flavoured foodstuff. The tomato juice thus aromatized presented a more natural top note when compared to the unflavoured material. It possessed as well a fresher and more fruity character than the latter.

C

A coffee drink was prepared by dissolving 1 g of commercial spray-dried coffee in boiling water. The beverage was then flavoured by adding to it at a concentration of 0.025 ppm, based on the weight of the flavoured material, 2-methyl-4-propyl-1,3-oxathiane. The thus flavoured beverage possessed a fuller taste of coffee and showed a more marked pleasant smoky-woody character.

D 100 g of "American blend" tobacco were sprayed with 2 g of a 0.01% solution of 2-methyl-4-propyl-1,3-oxathiane in 95% ethanol, and the tobacco thus flavoured was used to manufacture cigarettes. As a control, cigarettes were also manufactured from the same tobacco sprayed with 95% ethanol alone. The smoke from the cigarettes was subjected to organoleptic evaluation by a panel of flavour experts, who unanimously stated that the smoke of the flavoured cigarettes possessed a more marked "tobacco" character and a more pleasant note as compared with the smoke of the control cigarettes.

EXAMPLE 2

A base flavouring composition of the "Tutti-Frutti" type was prepared by admixing the following ingredients (parts by weight):

| | |
|---|---|
| Vanillin | 50 |
| Amyl butyrate | 20 |
| Benzyl acetate | 50 |
| Ethyl acetate | 100 |
| Orange oil | 100 |
| Citral | 120 |
| Benzyl alcohol | 440 |
| Total | 1000 |

Two flavour compositions were then prepared by mixing the following ingredients (parts by weight):

| | Flavour A (control) | Flavour B (test) |
|---|---|---|
| "Tutti-Frutti" base (as indicated above) | 100 | 100 |
| 2-Methyl-4-propyl-1,3-oxathiane at 0.1% in 95% ethanol | — | 25 |
| 95% ethanol | 900 | 875 |
| | 1000 | 1000 |

Flavour compositions A and B were then individually subjected to an evaluation by dissolving them, at a concentration of 0.10% by weight, in a sugar syrup prepared by dissolving 650 g of sucrose in 1000 ml of water. The majority of the taste panel members stated that the syrup flavoured with composition B presented an improved top note as well as a more fruity and fuller character as compared with the syrup flavoured with composition A.

EXAMPLE 3

A

A commercial compote was flavoured with 2-methyl-4-propyl-1,3-oxathiane-3-oxide at a concentration of 5 ppm based on the weight of the flavoured material. The flavoured foodstuff was then subjected to an evaluation by a panel of experienced tasters who stated that its taste was greener and more fruity than that of the unflavoured material. It possessed moreover a character reminiscent of rhubarb or green berries.

B

A commercial black-currant juice was flavoured with the said oxathiane-oxide at a concentration of 2 ppm. It was found that the typical black-currant character was thus enhanced.

C

By proceeding in an analogous way, a rhubarb compote was flavoured by using the said oxathiane-oxide at a concentration level of 3 ppm. The characteristic note of rhubarb was thus reinforced.

D

A coffee drink was prepared by dissolving 1 g of commercial spray-dried coffee in boiling water. The beverage was then flavoured by adding to it at a concentration of 1 ppm, based on the weight of the flavoured material, 2-methyl-4-propyl-1,3-oxathiane-3-oxide. The thus flavoured beverage possessed a fuller and richer taste of coffee and showed a slightly fruity character, typical for certain coffee qualities.

E 100 g of "American blend" tobacco were flavoured as indicated in Example 1 D. by using 2-methyl-4-propyl-1,3-oxathiane-3-oxide at a concentration level of 10 ppm, based on the total weight of the flavoured tobacco. The smoke of the thus manufactured cigarettes had a fuller taste and aroma of tobacco.

EXAMPLE 4

A base flavouring composition of "black-currant" type was prepared by admixing the following ingredients (parts by weight):

| | |
|---|---|
| Vanillin | 50 |
| Ethyl maltol | 10 |
| α-Ionone 10%* | 10 |
| Amyl acetate | 10 |
| Amyl butyrate | 20 |
| Eugenol | 20 |
| Buchu oil | 20 |
| Ethyl butyrate | 50 |
| Triacetin | 810 |
| Total | 1000 |

*in 95% ethanol

By using the above base composition, there were prepared two novel flavouring compositions by mixing the following ingredients (parts by weight):

| | Flavour A (control) | Flavour B (test) |
|---|---|---|
| "Black-currant" base composition (as indicated above) | 100 | 100 |
| 2-Methyl-4-propyl-1,3-oxathiane at 1% in 95% ethanol | — | 20 |
| 95% ethanol | 900 | 880 |
| | 1000 | 1000 |

The two above compositions A and B were evaluated by tasting them in an acidulated sugar syrup vehicle as indicated in Example 2 at a concentration of 0.1% by weight. The syrup flavoured with composition B has a fresher and more natural flavour character than that flavoured with composition A. Its taste was analogous to that developed by black-currant fruits.

EXAMPLE 5

Two base flavouring compositions of "grape-fruit" type were prepared by mixing together the following ingredients (parts by weight):

| | Flavour A (control) | Flavour B (test) |
|---|---|---|
| Grape-fruit oil | 200 | 200 |
| 2-Methyl-4-propyl-1,3-oxathiane at 0.1% in 95% ethanol | — | 25 |
| 95% Ethanol | 800 | 775 |

| | Flavour A (control) | Flavour B (test) |
|---|---|---|
| | 1000 | 1000 |

The above base compositions were tasted in an acidulated sugar syrup vehicle as indicated in Example 2. The foodstuff flavoured with composition B possessed a more marked "grape-fruit" character as well as a more juicy taste.

EXAMPLE 6

A base perfuming composition of "plum" type was prepared by mixing together the following ingredients (parts by weight):

| | |
|---|---|
| 2,6,6-Trimethyl-but-2-en-1-oyl-cyclohex-2-ene at 10%* | 400 |
| 1-(3,3-cyclohex-6-en-1-yl)-pent-4-en-1-one at 1%* | 200 |
| Dodecalactone | 150 |
| Decalactone | 100 |
| Menthyl acetate | 100 |
| Dimethyl-benzyl-carbinyl butyrate | 50 |
| Total | 1000 |

*in diethyl phthalate

By adding to 970 g of the above composition 30 g of a 1% solution of 2-methyl-4-propyl-1,3-oxathiane in diethyl phtahlate, there was obtained a novel composition the note of which had a more natural, refreshing and fruity plum character as compared to the base composition.

EXAMPLE 7

A base perfuming composition of "Chypre" type was prepared by mixing the following ingredients (parts by weight):

| | |
|---|---|
| Bergamot oil | 250 |
| α-iso-Methylionone | 60 |
| Synth. rose oil | 60 |
| Synth. Jasmin oil | 60 |
| Coumarin | 50 |
| Oriental Sandel-wood oil | 50 |
| Ylang oil | 40 |
| Musc ketone | 40 |
| Bourbon vetyver oil | 40 |
| Styrax resinoil 50%* | 30 |
| Absolute Oak-moss | 30 |
| Dodecanal 1%* | 30 |
| Hydroxycitronellal | 30 |
| Synth. civet 10%* | 30 |
| Labdanum resinoid 50%* | 30 |
| Undecenal 10%* | 20 |
| Musc ambrette | 20 |
| Synth. rose absolute | 20 |
| Synth. Jasmin absolute | 20 |
| Patchouli | 15 |
| Neroli Bigarade | 15 |
| Methyl-nonylacetaldehyde 1%* | 15 |
| Eugenol | 15 |
| Orris concrete | 10 |
| Tarragon | 10 |
| Vanillin | 10 |
| Total | 1000 |

*in diethyl phthalate

By adding to 990 g of the above base composition, 10 g of a 10% solution of 2-methyl-4-propyl-1,3-oxathiane in diethyl phthalate, there was obtained a novel composition which possessed an improved diffusiveness and a top note with a more defined fruity character than the base composition.

EXAMPLE 8

A

A natural black-currant juice was flavoured by adding to it trans 2-methyl-4-propyl-1,3-oxathiane-equatorial 3-oxide at a concentration of 5 ppm by weight, based on the weight of the flavoured material. The thus flavoured beverage possessed a more fruity, woody taste which conferred a more natural character as compared to the unflavoured material; the odour of the flavoured beverage was somewhat greener.

B

A natural passion fruit juice was flavoured by adding to it trans 2-methyl-4-propyl-1,3-oxathiane-equatorial 3-oxide at a concentration of 2.5 ppm. The flavoured beverage possessed as compared to the natural juice an enhanced fruity note as well as a more juicy character.

C

A canned natural grape-fruit juice was flavoured by adding to it trans 2-methyl-4-propyl-1,3-oxathiane-equatorial 3-oxide at a concentration of 5 ppm. The flavoured beverage possessed, as compared to the natural juice, a fresher and more fruit pulp character.

D

An instant onion soup was prepared by dissolving a commercial grade soup powder into boiling water. The thus prepared foodstuff was flavoured by adding to it cis 2-methyl-4-propyl-1,3-oxathiane-equatorial 3-oxide at a concentration of 1 ppm. The taste of the flavoured soup had more body and presented a fresher onion and meaty character as compared to the unflavoured material.

The Examples given hereinabove shall not be construed to restrict the scope of the present invention in any matter. By replacing the effective ingredients indicated therein by another one of the compounds defined by formula (I), namely those listed in the Table, analogous effects were observed. In some cases, however, by their use a more defined sulphury taste developed in the materials to which they are added, thus limiting the extent of their applications.

What is claimed is:

1. A composition comprising a compound of formula (I):

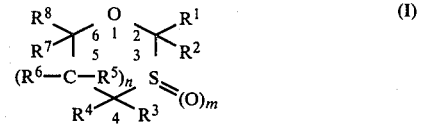

in which:
(a) m and n stand for zero or 1, and each of symbols $R^1$ to $R^8$ represents a hydrogen atom or a saturated or unsaturated, linear or branched alkyl radical containing from 1 to 11 carbon atoms, or
(b) n stands for 1 and m represents zero or 1, each of symbols $R^1$, $R^2$, $R^3$ and $R^4$ have the above described meaning, $R^5$ and $R^7$ each represents hydrogen and $R^6$ together with $R^8$ and the carbon atoms carrying them, in positions 5 and 6 respectively, form a substituted or unsubstituted cyclopentane or cyclohexane ring, or (c) n stands for 1 and m represents zero or 1, each of symbols $R^1$, $R^3$, $R^5$, $R^6$ and $R^7$ represents hydrogen, $R^2$ represents a lower alkyl radical or hydrogen atom, $R^4$ represents a para-substituted or unsubstituted phenyl or a substituted or unsubstituted cyclohexenyl radical, and $R^8$ stands for a lower alkyl, or (d) n stands for 1 and m represents zero or 1, each of symbols $R^1$, $R^3$, $R^5$, $R^6$ and $R^7$ represents hydrogen, $R^2$ a p-substituted or unsubstituted phenyl or a substituted or unsubstituted cyclohexenyl radical, $R^4$ represents a lower alkyl radical or a hydrogen atom, and $R^8$ stands for a lower alkyl or a hydrogen;

and a tobacco product.

2. A composition according to claim 1, in which said compound of formula (I) is in the form of one of its epimers or enantiomers.

3. A composition according to claim 1, in which said compound of formula (I) is in the form of a mixture of its epimers or enantiomers.

4. A method for modifying, improving or enhancing the organoleptic properties of tobacco products which comprises adding thereto a small but effective amount of at least one compound of formula (I), as defined in claim 1.

* * * * *